US007205401B2

(12) United States Patent
Bruening et al.

(10) Patent No.: US 7,205,401 B2
(45) Date of Patent: Apr. 17, 2007

(54) COMPOSITIONS AND METHODS FOR SEPARATING AMINES AND AMINO ACIDS FROM THEIR COUNTER-ENANTIOMERS

(75) Inventors: Ronald L. Bruening, American Fork, UT (US); Krzysztof E. Krakowiak, Provo, UT (US)

(73) Assignee: IBC Advanced Technologies, Inc., American Fork, UT (US)

( * ) Notice: Subject to any disclaimer, the term of this patent is extended or adjusted under 35 U.S.C. 154(b) by 268 days.

(21) Appl. No.: 10/664,045

(22) Filed: Sep. 16, 2003

(65) Prior Publication Data

US 2004/0132998 A1 Jul. 8, 2004

Related U.S. Application Data

(63) Continuation-in-part of application No. 09/802,123, filed on Mar. 8, 2001, now Pat. No. 6,686,479.

(60) Provisional application No. 60/411,251, filed on Sep. 17, 2002, provisional application No. 60/188,935, filed on Mar. 10, 2000.

(51) Int. Cl.
*C07D 267/22* (2006.01)
*C07D 471/02* (2006.01)
*C07D 321/00* (2006.01)

(52) U.S. Cl. .................. 540/456; 546/116; 549/348
(58) Field of Classification Search ................ 540/456; 546/116; 549/348
See application file for complete search history.

(56) References Cited

U.S. PATENT DOCUMENTS

| 4,001,279 | A | * | 1/1977 | Cram ........................ 549/348 |
|---|---|---|---|---|
| 4,043,979 | A | | 8/1977 | Cram |
| 4,943,375 | A | | 7/1990 | Bradshaw et al. |
| 4,952,321 | A | | 8/1990 | Bradshaw et al. |
| 4,959,153 | A | | 9/1990 | Bradshaw et al. |
| 4,960,882 | A | | 10/1990 | Bradshaw et al. |
| 5,039,419 | A | | 8/1991 | Bradshaw et al. |
| 5,071,819 | A | | 12/1991 | Tarbet et al. |
| 5,078,978 | A | | 1/1992 | Tarbet et al. |
| 5,084,430 | A | | 1/1992 | Tarbet et al. |
| 5,173,470 | A | | 12/1992 | Bruening et al. |
| 5,179,213 | A | | 1/1993 | Bradshaw et al. |
| 5,182,251 | A | | 1/1993 | Bruening et al. |
| 5,190,661 | A | | 3/1993 | Bruening et al. |
| 5,244,856 | A | | 9/1993 | Bruening et al. |
| 5,273,660 | A | | 12/1993 | Breuning et al. |
| 5,393,892 | A | | 2/1995 | Krakowiak et al. |

OTHER PUBLICATIONS

Armstrong, Daniel W., et al., *Capillary Electrophoretic Enantioseparations Using Macrocyclic Antibiotics as Chiral Selectors*, Electrophoresis, 1997, 18, pp. 2331-2342.
Armstrong, Daniel W., et al.; *Macrocyclic Antibiotics as a New Class of Chiral Selectors for Liquid Chromatography*; Analytical Chemistry, vol. 66, No. 9, May 1, 1994; pp. 1473-1484.
Armstrong, Daniel W., *Optical Isomer Separation by Liquid Chromatography*; Analytical Chemistry, vol. 59, No. 2, Jan. 15, 1987; pp. 84A-91A.
Bradshaw, Jerald S., et al.; *Enantiomeric Recognition of Organic Ammonium Salts by Chiral Dialkyl-Dialkenyl-, and Tetramethyl-Substituted Pyridino-18-Crown-6 and Tetramethyl-Substituted BIS-Pyridino-18-Crown-6Ligands: Comparison of Temperature-Dependent $^1$H NMR and Empirical Force Field Techniques[1]*; The Journal of Organic Chemistry, 1990, vol. 55; pp. 3129-3137.
Koshiishi, Ichiro, et al., *Simultaneous Determination of Vitamin C and its Carbamylated Derivatives by High-Performances Liquid Chromatography With Post-Column Derivitization*, Journal of Chromatography, 806 (1998) 340-344.
Kostrowicki, J., et al.; *Macrocyclic Polyfunctional Lewis Bases*; Journal of Chromatography, 454 (1988) 340-344.
P. Huszthy, et al., *Enantiomeric Separation of Chiral [A-(1-Naphthyl)Ethyl]Ammonium Perchlorate by Silica Gel-Bound Chiral Pyridino-18-Crown-6 Ligands*, Models in Chemistry 131 (3-4), pp. 445-454 (1994).
Pirkle, WH, et al. *Chiral Stationary Phases for the Direct LC Separation of Enantiomers*; Advances in Chromatography, 1987;27:73-127.
Pirkle, WH, et al.; *Considerations of Chiral Recognition Relevant to the Liquid Chromatographic Separation of Enantiomers*; Chem Rev., 1989, 89: 347-362.
Sogah, G. Dotsevi Yao, et al., *Chromotographic Optical Resolution Through Chiral Complexation of Amino Ester Salts by a Host Covalently Bound to Silica Gel*, Journal of the American Chemical Society, 1975, 97:5, pp. 1259-1261.
Sogah, G. Dotsevi Yao, et al., *Host-Guest Complexation. 14. Host Covalently Bound to Polystryrene Resin for Chromatographic Resolution of Enantiomers of Amino Acid and Ester Salts*, Journal of the American Chemical Society, 1979, 101, pp. 3035-3042.
Sogah, G. Dotsevo Yao, et al., *Total Chromatographic Optical Resolutions of α-Amino Acid and Ester Salts Through Chiral Recognition by a Host Covalently Bound to Polystyrene Resin*, Journal of the American Chemical Society, 1976, 98:10, pp. 1262-1265.
Taylor, Edward C., et al., *S-Alkylation and S-Acylation of the Thiocarbonyl Ligand in Metal Complexes*, Journal of the American Chemical Society, 1976, 98:10, pp. 1261-1262.
Zhang, et al.; *Enantiomeric Recognition of Amine Compounds by Chiral Macrocyclic Receptors*; Chemical Reviews, 1997, 97, 3313-3361.
Singh, Harjit, Subodh Kumar, Anupa Jain and Paramjit Singh, Synthetic Ionophores. Part 4. Phase Transfer—catalysed Synthesis of Pyridine-containing Macrocycles and Their Ionophore Character, J. Chem Soc. Perkin Trans. 1 1990.

* cited by examiner

*Primary Examiner*—Thomas McKenzie
*Assistant Examiner*—Raymond Covington
(74) *Attorney, Agent, or Firm*—Thorpe North & Western LLP

(57) ABSTRACT

Diketo- and pyridine-containing chiral crown ligands having at least two chiral bulky groups attached to two different chiral carbon atoms of the crown that are covalently bonded to or coated on suitable solid supports, and further coated by hydrophobic organic solvents are disclosed. These compositions and associated methods are characterized by selectivity of several target amine or amino acid enantiomers over their counter-enantiomers and derivatives. The composition preferably has an α-value greater than or equal to 4. This allows for the separation of such enantiomers with non-chromatographic resin bed separations of three separation stages or less.

35 Claims, No Drawings ly known in the literature. When these applications were made, much work had been done in the area of chiral separations, but few compositions were known which provide for high selectivity non-chromatographic separation of amines and amino acids from their counter-enantiomers. The inventors of the present invention have discovered new methods of chiral separations and related compositions, which provide high purity and throughput at a relatively low cost.

COMPOSITIONS AND METHODS FOR SEPARATING AMINES AND AMINO ACIDS FROM THEIR COUNTER-ENANTIOMERS

This application is a continuation-in-part of U.S. patent application Ser. No. 09/802,123 filed on Mar. 8, 2001 now U.S. Pat. No. 6,686,479, which is incorporated herein by reference in its entirety, which claims priority to U.S. Provisional patent application No. 60/188,935 filed on Mar. 10, 2000; this application also claims priority to U.S. Provisional Patent Application No. 60/411,251 filed on Sep. 17, 2002 which is incorporated herein by reference in its entirety.

FIELD OF THE INVENTION

The present invention is drawn toward compositions and methods for separating certain amine or amino acid target enantiomers from their counter-enantiomer in order to obtain a high degree of chiral purity.

BACKGROUND OF THE INVENTION

Effective methods for the separation and recovery of particular enantiomers of biochemicals such as amines and amino acids, as well as other types of biochemicals, is of great importance in modern technology. This importance is exemplified by the growing need and desire to produce and use optically pure pharmaceuticals and other biochemicals for human and other use. For example, often only one enantiomer of a chemical compound is biologically active or produces a desired effect. Thus, in order for a recipient of a pharmaceutical to receive enough of the biologically active enantiomer, twice the amount of pharmaceutical is generally given (assuming that the enantiomers are represented at about a 50:50 molar ratio). In other cases, an undesired enantiomer may be toxic or produce side effects. For example, the undesired enantiomer of thalidomide has been known to cause severe malformation in children born to pregnant women who took the drug by prescription for the benefits of the desired enantiomer. Therefore, much research has been conducted in order to produce optically or enantiomerically pure pharmaceuticals such that the biologically active or desired enantiomer may be used in essentially pure forms in order to eliminate the drawbacks discussed above.

There are essentially three theoretical methods that may be used to obtain optically pure compounds for pharmaceutical or other use. First, the desired enantiomer may be synthesized in the desired enantiomeric or optically pure form. Unfortunately this method is often impractical because, in many cases, these types of synthesis methods have not been discovered, or alternatively for those that have been discovered, the production cost of making the pure enantiomer has been prohibitive.

The second method involves separating the desired enantiomer from a mixture containing both enantiomers. However, because the enantiomers differ only in chirality, such processes have proven very difficult to carry out. In some instances, these separations have been accomplished by means of crystallization. For example, tartaric acid as a crystallization platform has been used for such a separation. Though this is a somewhat cost effective method, it is useful in only a minority of cases. In most instances, such separations must be performed using a chromatographic stationary phase and a chromatographic method of separation. These types of chromatographic separations have low throughputs and high operating costs.

The third method for chiral separation involves a combination of the two methods described above. In this combination method, an initial chiral intermediate is separated at a relatively high purity followed by additional synthesis steps that further purify the chiral intermediate to a final product without introducing additional chiral impurity.

In general, to overcome the high cost of performing chiral separations, a method that allows for high selectivity of a target enantiomer over its counter-enantiomer is needed. As such, non-chromatographic or equilibrium bind/release separation modes using solid resin phases have been formed to accomplish this result with several additional amines and amino acids that have not been easily separable in non-chromatographic form by previous resins. U.S. Publication No. 2002/0019491, filed on Mar. 8, 2001, the entirety of which is incorporated herein by reference, sets forth previous solid resin phases of sufficient selectivity and/or stability for the separation of several different amines and amino acids. Prior to this, there have not been compositions known to accomplish such an enantiomeric separation function to a degree of purity that is both practical to use and cost effective. This is significant because it is the separation itself that accounts for a large portion of the total cost of making a pure enantiomeric product. Thus, by reducing the separation costs, the final selling price of the pure enantiomer may be reduced.

As stated, some research has been done in producing chiral ligands capable of some selectivity between chiral enantiomers of the same compound. Additionally, electrophoresis has been used as well for such chiral separations. However, both of these methods, i.e. chromatography and electrophoresis, provide only low throughputs, and therefore, are not as desired as that described by the present invention. Some articles have described electrophoresis as a separation method and several other articles have discussed the use of such ligands in chromatographic resin phases. Such patents and articles include: U.S. Pat. Nos. 4,001,279 and 4,043,979 issuing to Cram, D. J.; Dotsevi, G., et al., *Chromatographic Optical Resolution through Chiral Complexation of Amino ester Salts by a Host Covalently Bound to Silica Gel*, J. Amer. Chem. Soc., 97:5, pp 1259–61 (1974); Bradshaw, J. S., et al., *Enantiomeric Recognition of Organic Ammonium Salts by Chiral Dialkyl-, Dialkenyl-, and Tetramethyl-Substituted Pyridino-18-crown-6 and Tetramethyl-Substituted Bis-pyridino-18-crown-6 Ligands: comparison of Temperature-Dependent H NMR and Empirical Force field techniques*, J. Org. Chem., Volume 55, pp. 3129–37 (1990); Zhang, et al., *Enantiomeric Recognition of Amine Compounds by Chiral Macrocyclic Receptors*, Chem. Rev., Volume 97, pp. 3313–61 (1997); Pirkle, W. H. et al., *Chiral Stationary Phases for the Direct LC Separation of Enantiomers*, Adv. Chromatography, Volume 27, pp. 73–127 (1987); Armstrong, D. W., et al., *Macrocyclic Antibiotics as a New Class of Chiral Selectors for Liquid Chromatography*, Anal. Chem., Volume 66, pp. 1473–1484 (1994); Armstrong, D. W., et al., *Optical Isomer Separation by Liquid Chromatography*, Anal. Chem., Volume 59, pp. 84A–91A (1987); Huszthy, P., et al., *Enantiomeric Separation of Chiral [α-(1-Naphth)Ethyl]Ammonium Perchlorate by Silica Gel-Bound Chiral Pyridino-18-Crown-6 Ligands*, Acta Chim Hung, Volume 131, pp. 445–54 (1994); Pirkle, W. H., et al., *Chem. Rev.*, Volume 89, pp. 347–362 (1989), all of which are incorporated herein by reference.

Outside of the work described in U.S. Publication No. 2002/0019491, high selectivity non-chromatographic separation of amines and amino acids via highly stable covalently attached or coated ligands in three separation stages or less has not been previously demonstrated. Most work in this area discloses procedures for synthesizing either chromatographic resin materials for chiral separations or for synthesizing unbound ligands with chiral selectivity in single phases. Therefore, it would be desirable to provide compositions and methods of separating enantiomers using non-chromatographic separation techniques that allow for much faster separations at much higher quantities while maintaining lower cost basis for the separation. Though U.S. Publication No. 2002/0019491 describes effective non-chromatographic separations for several chiral amines and amino acids, it has since been found that certain β-amino acids and/or large α-amines containing aromatic groups can be separated even more efficiently using particular solvent-coated ligand-bound solid supports not described previously.

SUMMARY OF THE INVENTION

The present invention is drawn to compositions and methods for separating chiral amine and amino acid target enantiomers over their counter-enantiomers. In one embodiment, a composition for selectively binding a chiral amine or amino acid enantiomer over its counter-enantiomer can comprise a solid support, an optically active ligand tethered to or coated on the solid support, and a hydrophobic organic solvent coating coated on the solid support. The optically active ligand tethered to or coated on the solid support can have the structure of Formula 1 below:

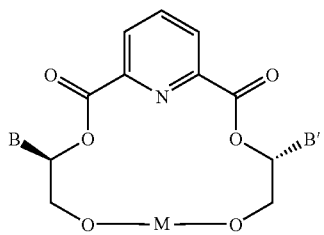

Formula 1 where B and B' are independently bulky groups; and M is saturated —$C_2H_3$— or saturated —$C_2H_3OC_2H_4$— when M is tethered to the solid support, or M is saturated —$C_2H_4$— or saturated —$C_2H_4OC_2H_4$— when M is coated on the solid support.

In another embodiment, a non-chromatographic method for concentrating, removing, and separating a chiral amine or amino acid enantiomer from its counter-enantiomer in a source solution containing an enantiomeric mixture can comprise several steps. Such steps include contacting the source solution with the composition of Formula 1, wherein the composition has an affinity for a chiral amine or amino acid target enantiomer over its counter-enantiomer, and wherein upon contacting, the target enantiomer is complexed to the composition. Further steps include removing the source solution from contact with the composition to which the target enantiomer has been complexed, contacting the composition having the target enantiomer complexed thereto with a second volume of an aqueous receiving solution such that the target enantiomer is separated from the composition, and recovering the target enantiomer in concentrated form in the receiving solution.

In another embodiment, a non-chromatographic method of separating an enantiomeric molecule from its counter-enantiomer can comprise several steps. Such steps include flowing a racemic feed solution containing a target enantiomer and its counter-enantiomer through a separation device, wherein the separation device includes a first composition as set forth in Formula 1, and wherein the first composition has an affinity for the target enantiomer and a selectivity of at least 4. Additional steps include selectively forming a complex between the target enantiomer and the first composition, thereby forming a first raffinate having increased purity of the counter-enantiomer; breaking the complex between the target enantiomer and the first composition with a second volume of an aqueous receiving solution to form a target enantiomer enhanced receiving liquid; and flowing the target enantiomer enhanced receiving liquid through a second separation device, wherein the second separation device includes a second composition having the structure of Formula 1, but having an opposite optical activity compared to the first composition. An additional step includes selectively forming a complex between the counter-enantiomer and the second composition in the second separation device, thereby forming a second raffinate having increased purity of the target enantiomer.

Additional features and advantages of the invention will be apparent from the following detailed description which illustrates, by way of example, features of the invention.

DETAILED DESCRIPTION OF THE PREFERRED EMBODIMENT(S)

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting.

It must be noted that, as used in this specification, the singular forms "a," "an," and "the" include plural referents unless the content clearly dictates otherwise.

"Racemate" or "racemic" when referring to feed solutions is intended to include any solution containing both enantiomeric varieties of a molecule, i.e. the enantiomer and counter-enantiomer, in approximately equal amounts. The solution may also contain other matter including other contaminants or impurities that are desired to be separated out.

"Raffinate" is intended to include the solution that passes through the separation device excluding the molecules or enantiomers that bind to the ligands attached to or coated on the solid supports. In some instances, the raffinate will contain the target enantiomer in high concentration and in some instances the raffinate will contain the target enantiomer in low concentration, depending on whether the ligand is optically designed to bind to the target enantiomer or the counter-enantiomer.

"Counter-enantiomer" generally shall include the chiral molecule that is to be separated out from the target chiral enantiomeric molecule. In some embodiment, the target enantiomer can be the only composition desired for collection, and in others, both the target enantiomer and the counter-enantiomer can desired for separate collection.

"Target enantiomer" or "desired enantiomer" generally shall include the chiral molecule that the compositions and methods of the present invention are designed to purify or collect. The counter-enantiomer in one separation may be the target enantiomer of another separation, depending on the goals of the separation.

"Ligand-bound solid support" can include optically active ligands in accordance with the present invention that are either tethered to, or coated on, conventional solid supports. If tethered, the attachment mechanism is typically a covalent attachment. If coated, the coating is typically a solid coating on the surface of the solid support. In either embodiment, the resulting ligand-bound solid support can be further coated with an organic solvent to achieve the selectivity described herein.

The phrase "coated on" when referring to the optically active ligand and/or the hydrophobic organic solvent coating does not infer that it must be coated directly on the material it refers to. For example, by stating that an optically active ligand and a hydrophobic organic solvent are coated on a solid support, the optically active ligand can be coated directly on a solid support, and a hydrophobic organic solvent coating can be coated directly on the optically active ligand coating. Both would be considered to be coated on the solid support. Alternatively, a single coating composition that includes both the optically active ligand and the hydrophobic organic coating can be coated on the solid support. This latter embodiment can occur if, for example, the ligand is dissolvable in the hydrophobic coating solvent.

The term "coated" or "coating" refers to a substance that is applied to a surface to form at least one stationary layer of material on the surface. A continuous flow of a substance over a surface, such as is the case with a mobile phase in chromatography, is not considered to be a coating.

The term "bulky group" includes branched or unbranched alkyl groups of from 3 to 10 carbons, as well as aromatic groups. An example of a branched alkyl bulky group that is effective for use is t-butyl. Examples of aromatic groups that can be used include naphthyl, pyridyl, anthracyl, phenanthryl, benzonaphthyl, and phenyl. A function of the bulky groups is to substantially allow one enantiomer of a chiral amine or amino acid to bind to the composition, as well as substantially sterically hinder a counter-enantiomer of the amine or amino acid from binding to the composition. As chiral molecules can approach the composition from either above or below the pyridine crown, it is helpful to provide symmetry with respect to steric hindrance so that chiral separations can occur no matter what angle the amine or amino acid approaches the composition. For example, as a chiral amine or amino acid approaches and attempts to bind itself on one side of the pyridine crown, one of the bulky groups provides steric hindrance to the counter-enantiomers of a racemic or other mixture, and at the same time, does not hinder the target enantiomer from attaching. If the amine or amino acid approaches and attempts to bind to the other side of the pyridine crown, the other bulky group also provides steric hindrance to the counter-enantiomer of the mixture, thus allowing for the target enantiomer to selective bind thereto.

With these definitions in mind, the invention described herein provides for a sufficiently stable and selective solid resin phase composition and related methods for the separation of target chiral amines and amino acids from their counter-enantiomers. These compositions are particularly useful for the separation or chiral amines and amino acids such as β-amino acids and aromatic α-amines. Unlike much of the prior art in this area, the separations of the present invention may be carried out utilizing highly desirable and cost effective non-chromatographic separation methods.

The composition is essentially an optically active diketo- and pyridine-containing crown ligand tethered to or coated on a solid support, wherein the ligand-bound solid support is coated with a hydrophobic solvent, thereby forming a highly selective (selectivity factors greater than or equal to 4) non-chromatographic separation resin compound. The compound enables one to separate target chiral amines, chiral amino acids, and their derivatives from their counter-enantiomers. The resin compounds of the present invention are highly stable, and thus, may be reused on multiple occasions. Additionally, not only can this composition be used for removing, separating, and/or concentrating certain target chiral amines or amino acids from their counter-enantiomers, other impurities as well which might be present can also be separated out.

The composition for selectively binding an amine or amino acid target enantiomer over its counter-enantiomer can comprise a solid support, an optically active ligand tethered to or coated on the solid support, and a hydrophobic organic solvent coating coated on the solid support. The optically active ligand tethered to or coated on the solid support can have the structure of Formula 1 below:

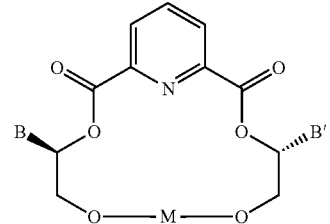

Formula 1 where B and B' are independently bulky groups; and M is saturated —$C_2H_3$— or saturated —$C_2H_3OC_2H_4$— when M is tethered to the solid support, or M is saturated —$C_2H_4$— or saturated —$C_2H_4OC_2H_4$— when M is coated on the solid support. The reason that one less hydrogen is present in the formula with respect to the tethering embodiment relates to the fact that a hydrogen atom is typically replaced when the solid support is chemically attached to the ligand. In other words, the missing hydrogen indicates the location of attachment. In one embodiment, the bulky groups (B and/or B') can be independently selected from the group consisting of aromatic, lower branched alkyl having from 3 to 10 carbon atoms, and lower straight alkyl having from 3 to 10 carbon atoms. For example, in embodiments where the bulky groups (B and/or B') are aromatic, from 1 to 6 ring structures can be present. Examples of preferred aromatic rings include phenyl, naphthyl, pyridyl, anthracyl, phenanthryl, and/or benzonaphthyl. When the bulky groups (B and/or B') are branched alkyl, t-butyl can provide good steric hindrance.

As stated, the composition can comprise a ligand coated on a solid support, or can comprise a ligand tethered to a solid support. If the ligand is coated on the solid support, the composition can be represented by Formula 2a as follows:

SS-L

Formula 2a wherein the bond shown between SS and L represents a physical bond or coating, rather than a chemical bond. In accordance with this formula, SS can be a porous or non-porous particulate inorganic or organic polymer solid support, and L can be a diketo- and pyridine-containing crown ligand molecule having two bulky groups attached to chiral carbons in the crown ligand molecule, such as described in Formula 1.

If the ligand is tethered to the solid support, the ligand to solid support attachment can be through a hydrophilic spacer as shown in Formula 2b below:

Formula 2b

In Formula 2b, SS can be a porous or non-porous particulate inorganic or organic polymer solid support, A can be a covalent linkage mechanism, X can be a hydrophilic spacer grouping, and L can be the diketo- and pyridine-containing chiral crown ligand molecule having two bulky groups attached to chiral carbons of L, such as that shown in Formula 1. Further, when SS is a particulate organic polymer, A-X may be combined as a single covalent linkage.

The ligand-bound solid support (SS-L or SS-A-X-L) is preferably coated with a hydrophobic organic solvent. Exemplary hydrophobic solvents that can be used include methylene chloride, chloroform, dichloroethane, benzene, toluene, xylene, hexane, and/or octane, though other hydrophobic solvents may be used. This coating can be applied subsequently to the preparation of the ligand-bound solid support, or can be applied simultaneously with the preparation of the ligand-bound solid support. For example, a coating composition that includes both the optically active ligand and the hydrophobic organic solvent can be coated as a single coating. In Formulas 2a and 2b, though only one ligand is shown tethered to or coated on one solid support, it is understood that multiple ligands will likely be present on each solid support.

The SS-portion of Formula 2a, and each component of the SS-A-X-portion of Formula 2b are well known for use with ion binding ligands. Preferably, solid support (SS) can be an inorganic and/or organic particulate support material selected from the group consisting of silica, silica gel, silicates, zirconia, titania, alumina, nickel oxide, glass beads, phenolic resins, polystyrenes and polyacrylates. However, other organic resins or any other hydrophilic organic and/or inorganic support materials meeting the above criteria can also be used. Because the invention provides for the coating of the ligand-bound solid support with an organic solvent, organic solid supports such as phenolic resins, polystyrenes and polyacrylates tend to perform better. However, both inorganic supports and organic solid supports are both certainly functional.

The use of organic ion binding ligands attached to an SS-A-X- solid support by means of a covalent linkage spacer grouping is illustrated in U.S. Pat. Nos. 4,943,375; 4,952,321; 4,959,153; 4,960,882; 5,039,419; 5,071,819; 5,078,978; 5,084,430; 5,173,470; 5,179,213; 5,182,251; 5,190,661; 5,244,856; 5,273,660; and 5,393,892. These patents, which disclose various spacers that can be used in forming an organic ligand attached to a solid support, are incorporated herein by reference.

If an inorganic solid support is used, and covalent attachment or tethering is implemented, a hydrophilic spacer can be grouped to a silicon, carbon, nitrogen, oxygen, or sulfur atom and can further be covalently bonded to a particulate porous and/or non-porous solid support. When the solid support SS is an inorganic material such as silica, silica gel, silicates, zirconia, titania, alumina, nickel oxide, and/or glass beads, the covalent linkage A can be a silane such that A-X may be represented by Formula 4 below:

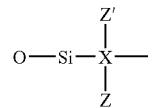

Formula 4 wherein Z and Z' can independently represent members selected from the group consisting of Cl, Br, I, lower alkyl, lower alkoxy, substituted lower alkyl or substituted lower alkoxy, and O-SS (where SS represents the solid support of Formula 2b). As used herein, lower alkyl or lower alkoxy means a group having 1 to 16 carbon atoms. Alternatively, functional siloxanes can be used as well.

Additionally, X can be a spacer grouping in accordance with Formula 5 below:

Formula 5 wherein $R^1$ is a member selected from the group consisting of H, SH, OH, lower alkyl, and aryl; a is an integer from 3 to about 10; and b is an integer of 0 or 1.

If an organic polymer or resin solid support is used in a tethering embodiment, i.e. SS is a particulate polymeric organic solid support matrix such as polyacrylate, polystyrene, and/or polyphenol, the ligand can generally contain a functional grouping reactive with an activated polar group on the polymer. When the A and X are combined, they may be represented by Formula 6 below:

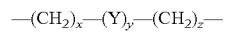

Formula 6 where y can be 0 or 1; x and z can independently be whole numbers from 0 to 10; and Y can be a member selected from the group consisting of O, S, C=N, CO, CONH, CSNH, COO, CSO, NH, NR, SO, $SO_2$, $SO_2NH$, $C_6H_4$, and $CH_2C_6H_4$ where R can be lower alkyl, with the proviso that at least one of x, y and z must be at least 1.

It is to be emphasized that the present invention does not reside in the discovery of the SS-A-X- or SS-portion of Formula 2a and 2b above. Rather, it is the discovery that the optically active diketo- and pyridine-containing crown ether ligands covalently bonded to solid supports and coated with a hydrophobic solvent exhibits the ability to non-chromatographically separate enantiomers of particular chiral amines and/or chiral amino acids. Further, the invention is not limited to compositions and methods that specifically use the SS-L or SS-A-X-L formulas, as other tethering or coating schemes can be used that are not specifically set forth herein. For example, with respect to the ligand (L) coating embodiments, the ligand (L) can be coated on the solid support (SS) with a third composition, or on top of a third composition. A method of the present invention involves utilizing up to three separation stages in a non-chromatographic mode of operation, thus, greatly increasing the product throughput and economic efficiency of any given system despite its size. Fewer stages can be used in some embodiments. More particularly, the method for separating such target amine or amino acid enantiomers from an admixture containing the counter-enantiomer of the chiral amine and/or chiral amino acid (and other non-desired chemicals or particulates) in a common solution can be carried out by selectively forming a complex between the target amine or amino acid enantiomer with the compositions of the present invention described above. These compositions have at least a selectivity factor of 4 in each of up to three separation stages, though one or two separation stages is also functional and within the scope of this invention.

The separation is effectuated by attaching (or coating) diketo- and pyridine-containing chiral crown ether ligand solid supports, such as those shown in Formula 1, and coating the ligand-bound solid support with a hydrophobic solvent. Such a coated composition can be used in a separation device such as a column, wherein the separation can occur by flowing a source solution containing a mixture of two enantiomers of a chiral amine and/or chiral amino acid through a support mass of the composition. Specifically, the steps of one method can include (1) flowing the mixture containing the target enantiomer and its counter-enantiomer (carried by a solvent such as an alcohol or water) through a column packed with the optically active diketo- and pyridine-containing crown ether ligand-bound solid supported materials (such as in Formula 1) coated with a hydrophobic solvent, (2) allowing the composition to selectively complex with the target enantiomer, and (3) breaking the complex of the target enantiomer from the compound to which the target enantiomer has become attached by flowing a complex breaking receiving liquid in smaller volume than the volume of solution originally passed through the column to remove and concentrate the target enantiomer in solution in the receiving liquid. At this point, a first separation has been effectuated.

Next, the receiving liquid containing a more concentrated amount of the target enantiomer can then be adjusted with solvent addition and/or salt addition to a state where the target amine or amino acid enantiomers are again capable of binding to the solid supported ligands. The adjusted solution is then run through a separation device containing a diketo- and pyridine-containing chiral crown ether ligand of opposite optical or chiral activity (such as in Formula 1) bonded to the solid support and coated with a hydrophobic solvent. Thus, the counter-enantiomer is now selectively bound in a non-chromatographic mode to the composition of opposite optical activity, and a large portion of the remaining counter-enantiomer is removed from the raffinate. In other words, the process of complexation in the second stage is similar to that for the initial separation stage, except that the bound ligand used is of the opposite chirality. The second stage may be repeated by again utilizing the ligand of the opposite chirality, thus leading to an even greater purity. Whether or not a second stage, or subsequent second stage separations, is needed will largely depend on the $\alpha$-value and desired purity. A reason that it is desirable to conduct the first stage of separation by binding the target enantiomer to the composition in the separation device is due, in part, to the fact that the counter-enantiomer can be removed along with other undesired chemicals or particulates in the first stage of separation. If one were to engineer the separation such that the target enantiomer was obtained in the raffinate after the first stage, then other impurities would remain present with the target enantiomer. However, though conducting a separation that begins with collecting the target enantiomer in the raffinate is less desirable from an engineering perspective, it is still within the scope of the present invention.

An $\alpha$-value of 4.0 indicates a four-fold preference for one enantiomer over its counterpart. Thus, if one is dealing with an $\alpha$-value of 4.0, then three separations are needed to achieve a 98.5% purity of one enantiomer over the other, assuming a racemic starting solution. Larger $\alpha$-values lead to either greater purity and/or fewer separation stages. Technologies that can use at capacity or near full capacity of the active material and that can achieve substantial separation in three or less stages can offer significant process benefits both economically and from an engineering perspective. Table 1 below shows a sample of enantiomeric purity obtained as a function of various $\alpha$-values at various numbers of separation stages for the non-chromatographic system of the present invention, assuming a racemic composition is provided for use in stage one.

TABLE 1

| $\alpha$-VALUE | NUMBER OF STAGES | PURITY OBTAINED (%) |
|---|---|---|
| 4 | 1 | 80 |
| 4 | 2 | 94.1 |
| 4 | 3 | 98.5 |
| 6 | 1 | 85.7 |
| 6 | 2 | 97.3 |
| 6 | 3 | 99.5 |
| 8 | 1 | 88.9 |
| 8 | 2 | 98.5 |
| 8 | 3 | 99.8 |
| 10 | 1 | 90.9 |
| 10 | 2 | 99.0 |
| 20 | 1 | 95.2 |
| 20 | 2 | 99.8 |

From this table, it is apparent that the higher the $\alpha$-value, the fewer the number of separation stages required to reach 99% enantiomeric purity. For an $\alpha$-value of 5 (not shown), the use of only three stages allows one to obtain >99% purity.

If desired, the process also allows for recovery of any of the target amines or amino acids that were not collected during the first stage of separation, i.e. bleed through of the target enantiomer of the chiral amine and/or chiral amino acid. As mentioned, the solution that remains after most of the target amine or amino acid material has been collected during stage one is called the raffinate. The raffinate containing a minority of the target amine or amino acid from the initial separation stage may be treated by passing the raffinate through an additional column(s), and thus, remove a portion of the target enantiomer from the raffinate. Though it is not required, the use of a smaller amount of the resin containing a coated optically active ligand-bound solid support with selectivity for the target amine or amino acid may be desired to collect the target amine or amino acids that were not collected during the initial separation stage. Once this is completed, the remainder of the process is similar to the initial separation stage.

Though the compositions and methods describe a preferred system of separation, i.e. three separation stages utilizing ligands of alternating chiralities between the first and second/third stages, other systems may be developed utilizing these principals. For example, one may design the composition such that the counter-enantiomer in the first column separation is bound to the ligands. Thus, the raffinate would contain the majority of the target molecular enantiomer, though the use of such a method can leave impurities in the raffinate with the target enantiomer. To alleviate this, a subsequent stage where the target enantiomer is bound to the resin can be carried out. These and other combinations of separations are within the scope of the invention. Additionally, the size of the optically active ligand can be adjusted within the parameters described in order to functionalize or modulate the separation device for maximum efficiency. For example, larger macrocycles can be used for the separation of larger molecules. Crown-5 and crown-6 optically active ligands such as those shown in Formula 1 are the most preferred ligands for use. When investigating the suitability of a particular resin-bound separation process, the following factors can be considered: (1) resin consumption; (2) solvent usage; (3) productivity, e.g., chemical, optical, and volume yield; (4) total number of separation steps; and (5) capital costs. The non-chromatographic separation method of the present invention compares favorably to current industry practice. For example, the compositions and methods of the present invention provide reduced number of process steps; high chemical, optical, and volume yields; high feed throughput; more open-ended solvent choice; minimized solvent usage; and low resin consumption.

Reduced number of process steps are achieved in part due to the fact that the ligands of the present invention display both high chemo- and enantio-selectivity, allowing for simultaneous chiral resolution and chemical separation. High chemical, optical, and volume yields are achieved due to the large capacity of the ligands of the present invention for a single enantiomer on each load cycle. The high selectivity also results in high yield throughputs and close to 100% time usage of the system for feed introduction. Additionally, because the ligands of the present invention are bound to solid supports as described, the covalent linkage provides for long life and multiple recycling capabilities. This feature also allows the user to choose the best solvent for the specific results desired, thus, the solvent choice is deemed open ended. Because high feed concentrations can be used and because feeds can be flowed through nearly continuously, the amount of solvent used may be drastically reduced. Also, because of the highly efficient use of the capacity of the ligand-bound solid supports as well as their high stability, there is low resin consumption. Conversely, with chromatographic techniques, low yields and high solvent consumption are often realized.

The chiral separations described in the present invention have many possible applications. For example, in the pharmaceutical industry, these separations may be used for analysis, drug development, and commercial production. During the drug discovery process, extensive screening of available compounds is performed along with animal testing. Thus, small quantities of optically pure drug are often needed quickly to screen candidates. Matrix versatility and rapid throughput are often also essential. Additionally, during pre-clinical and clinical development stages, the requirements for optically pure drug quantities can increase dramatically, e.g., from several grams to 100 kilograms. Optically pure drugs can also be needed for animal studies, e.g., pharmacokinetics, metabolism, tissue distribution, and safety, and human clinical studies in Phases I, II, and III. Again, time is often critical in these studies, thus, a rapid separation system as described herein would be advantageous. Further, during product launch and production, large amounts of racemate, i.e. >25 tons/year, with total process costs well under the targeted kg drug product prices are important to these industries.

Amino acid separation represents another specific application of the present invention. Amino acids are important synthesis precursors (in particular for pharmaceuticals) such as, for example, D-phenylglycine or D-parahydroxyphenylglycine in the preparation of semisynthetic penicillins. They are also used for other chiral fine chemicals and for incorporation into modified biologically active peptides. Since the unnatural amino acids cannot be obtained by fermentation or from natural sources, they must be prepared by conventional synthesis followed by racemate resolution, by asymmetric synthesis, or by biotransformation of chiral or prochiral precursors. Specialized types of amino acids for synthesis applications represent a growing field in the biotechnology industry. Applications include peptide hormones and growth factors, immunologic antigens, enzyme substrates, receptors and ligands, chemical drugs, bioactive peptides for research, combinatorial chemistry, drug discovery, pesticides, and artificial sweeteners, to name a few. Thus, amino acids represent an important class of compounds that can benefit from more efficient separation technologies. Amines and amino esters are also important in both chiral final materials and intermediates.

EXAMPLES

The following examples illustrate preferred embodiments of the invention that are presently best known. However, other embodiments can be made and are within the scope of the present invention.

Preparation of Ligand-Bound Solid Supports

Example 1

Preparation of di-tert-butyl-diketo-pyridine-18-crown-6 tethered to polystyrene 4S, 14S-(+)-4,14-Di-tert-butyl-3,6,9,12,15-pentaoxa-21-azabicyclo[15.3.1]heneicosa-1 (21),17,19-triene-2,16-dione attached through a side arm to polystyrene (composition 5 below) can be prepared as follows:

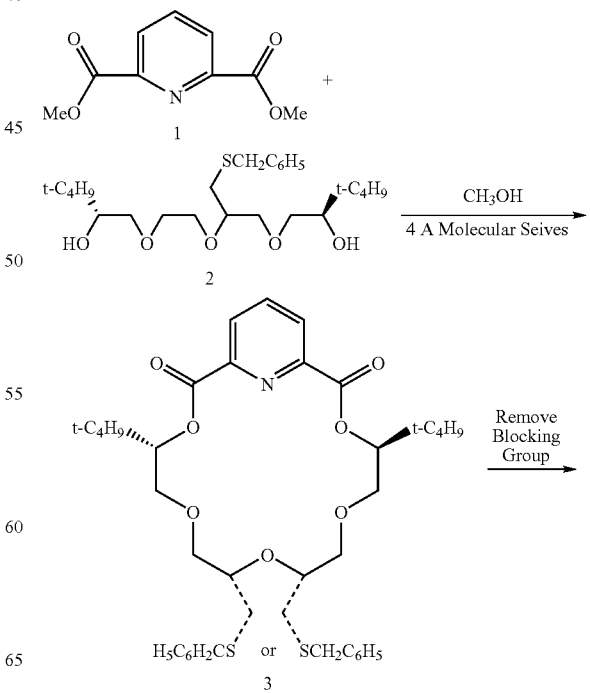

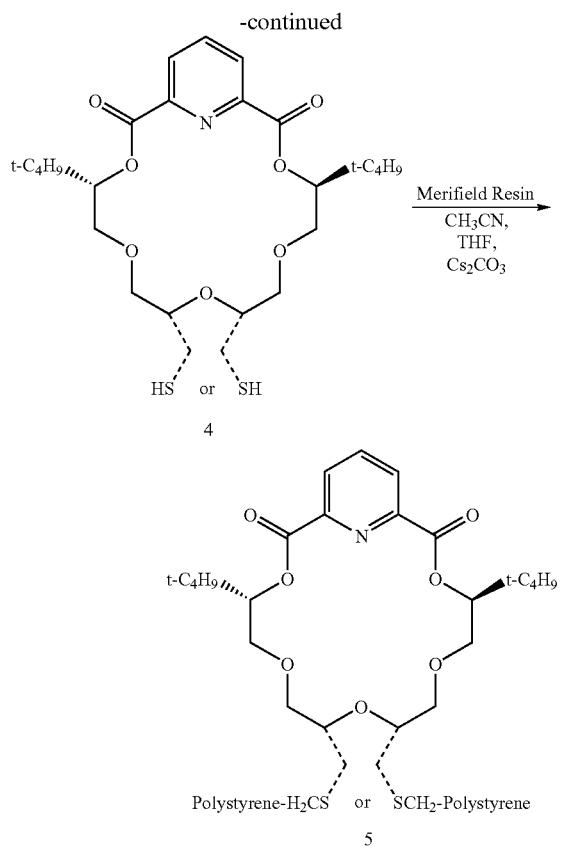

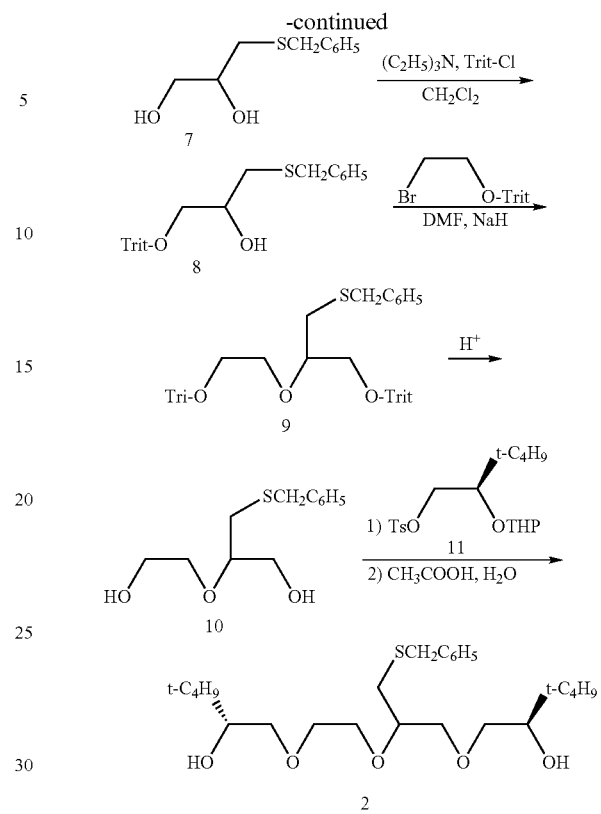

In the above reaction scheme, composition 1, which is commercially available, and composition 2 are reacted by a condensation reaction process in the presence of molecular sieves and methanol. This condensation reaction forms a pyridine-18-crown-6 as shown in composition 3. The blocking group can then be removed by conventional methods to form a second pyridine-18-crown-6 as shown in composition 4. Composition 4 can then be reacted with cesium carbonate and chloromethylpolystyrene in THF to form the di-tert-butyl-diketo-pyridine-18-crown-6 bound to polystyrene shown in composition 5.

As a side note, the side arms can be different than that shown above. For example, —(CH$_2$)$_n$O—, —(CH$_2$)$_n$N—, or —(CH$_2$)$_n$S—, can be used, where n is an integer from 1 to 18. Alternatively, branched alkyl-O, branched alkyl-N, or branched alkyl-S can also be used, having from 1 to 18 carbon atoms. Additionally, the dotted lines are used to show two possible side arm linkers attaching the crown to the polystyrene. Both are provided as shown in composition 5 to denote two possible equivalent isomers. Both isomers can be present in roughly equal proportions, though whatever the proportion, the effectiveness for effecting separations is substantially unaffected. Additionally, though less preferred, both linker arms can be present on a single crown molecule.

In order to carry out the reaction steps shown above, composition 2 is formed by the following reaction steps:

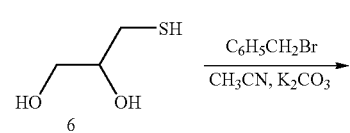

In the above reaction scheme, composition 6 can be treated with benzyl bromide in acetonitryle in the present of potassium carbonate to form composition 7. Trityl chloride is then reacted with composition 7 in the presence of triethylamine in methylene chloride. The mono-protected diol of composition 8 that is formed can then be reacted with 2-bromoethanol protected by trityl groups and sodium hydride in DMF at room temperature to produce composition 9. The trityl groups can be removed from composition 9 (thereby removing the protection they provide) by a reaction with hydrogen ions to form composition 10. Composition 11 can then be reacted with composition 10 to form composition 2 after removing the THP blocking group. In the above reaction scheme, the preparation of composition 11 is described in *J. Org. Chem.*, 1991 (56) 3330, which is incorporated herein by reference.

Example 2

Preparation of diphenyl-diketo-pyridine-18-crown-6 tethered to polystyrene 4S,14S-(−)-4,14,Diphenyl-3,6,9,12,15-pentaoxa-21-azabicyclo[15.3.1]heneicosa-1(21),17,19-triene-2,16-dione attached through a side arm to polystyrene (Composition 16 below) can be prepared as follows:

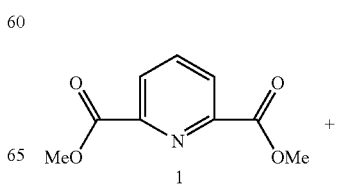

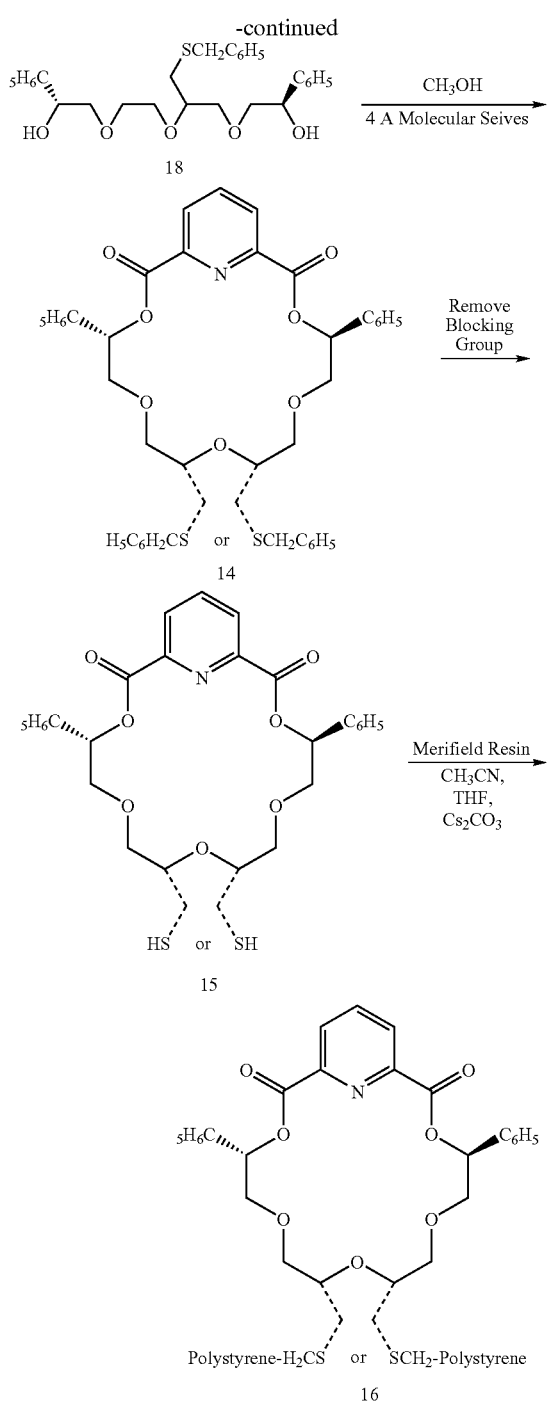

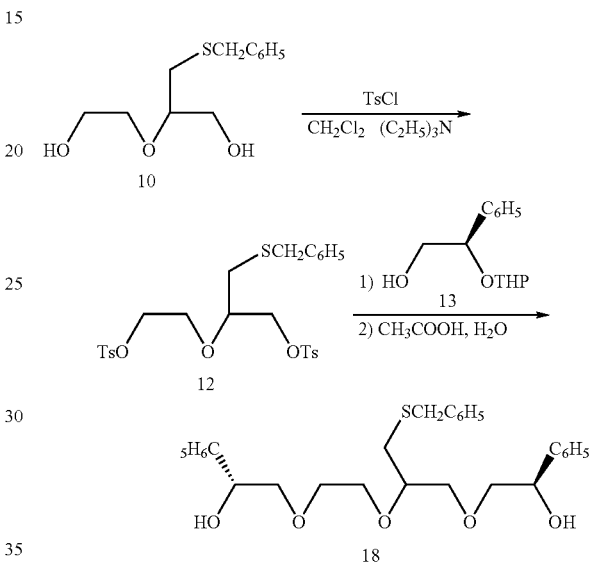

In the above reaction scheme, composition 16 is prepared by, first, carrying out a condensation reaction between composition 1 and composition 18 in methanol in the presence of molecular sieves, resulting in the pyridine-18-crown-6 of composition 14. Composition 14 can then be deprotected to form composition 15 by conventional methods. Composition 15 can then be reacted with cesium carbonate and chloromethyl polystyrene in a mixture of acetonitrile and tetrahydrofuran to form composition 16.

As a side note, the side arms can be different that that shown above. For example, —$(CH_2)_nO$—, —$(CH_2)_nN$—, or —$(CH_2)_nS$—, can be used, where n is an integer from 1 to 18. Alternatively, branched alkyl-O, branched alkyl-N, or branched alkyl-S can also be used, having from 1 to 18 carbon atoms. Additionally, the dotted lines are used to show two possible side arm linkers attaching the crown to the polystyrene. Both are provided as shown on composition 16 to denote two possible equivalent isomers. Both isomers can be present in roughly equal proportions, though whatever the proportion, the effectiveness for effecting separations is substantially unaffected.

In order to carry out the reaction steps shown above, composition 18 can be prepared by the following reaction steps:

This preparation can occur by, first, reacting composition 10 (as prepared in Example 1) with tosyl chloride in the presence of triethylamine in methylene chloride to form composition 12. Composition 13, can be produced in accordance with *J. Het. Chem.*, 1984, (21), 897 and *J. Org. Chem.*, 1991, (56), 3330, both of which are incorporated herein by reference. Composition 12 can be reacted with composition 13 as shown to form composition 18 after deprotection using acetic acid.

Example 3

Preparation of di-tert-butyl-diketo-pyridine-15-crown-5 tethered to polystyrene 4S,11 S-4,11-Di-tert-butyl-3,6,9,12-tetraoxa-18-azabicyclo[12.3.1]oxtadecane-(18), 14,16-triene-2,13-dione attached through a side arm to polystyrene (Composition 21 below) can be prepared as follows:

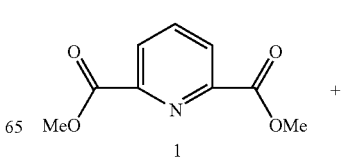

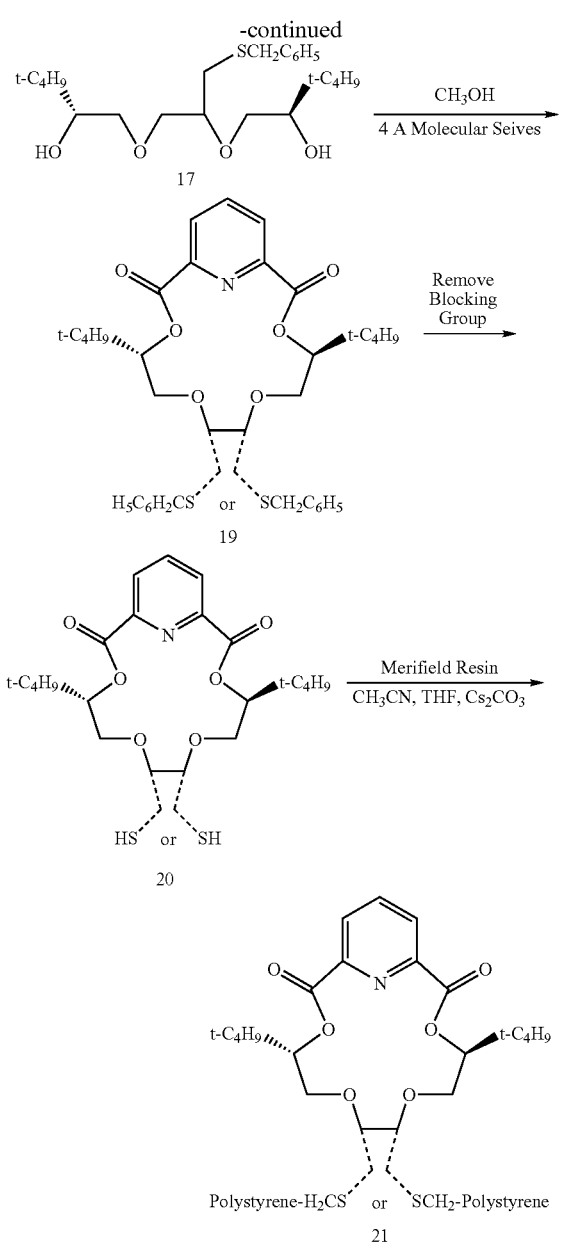

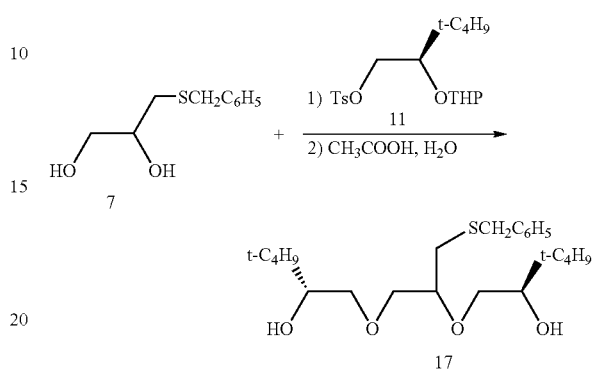

be present in roughly equal proportions, though whatever the proportion, the effectiveness for effecting separations is substantially unaffected.

In order to carry out the reaction steps shown above, composition 17 can be formed by the following reaction steps:

In the above reaction scheme, compound 17 can be prepared by reacting composition 7 with composition 11 following deprotection with acetic acid. The preparation of composition 11 is described in *J. Org. Chem.*, 1991 (56) 3330, which is incorporated herein by reference.

Example 4

Preparation of diphenyl-diketo-pyridino-18-crown-6 coated on polystyrene

A 7.58 g amount of CMP-11 polystyrene was suspended in 100 ml of $CH_2Cl_2$ for 30 minutes. The resin was then filtered on filter paper and washed on the filter four times with 50 ml of $CH_2Cl_2$, and then was room temperature air-dried overnight. About 2.5 g of the chiral diphenyl-diketo-pyridine-18-crown-6 was then dissolved in 30 ml of $CH_2Cl_2$. The chiral crown in $CH_2Cl_2$ was then mixed with the washed polystyrene gently for 1 hour. The excess solvent (not on beads) was then allowed to evaporate. Excess water was then added to the coated resin to cover the coated beads and prevent further evaporation of the $CH_2Cl_2$ used in the coating process. The resulting product is a polystyrene solid support coated with a diphenyl-diketo-pyridino-18-crown-6.

In Examples 1–4 above, the ligand-bound solid support form can then be coated with a hydrophobic organic solvent by one of many processes, including dipping, evaporating, and flowing the organic solvent past the resin in a packed column.

The preparation of composition 21 above is carried by first, a condensation reaction between composition 1 and composition 17 in methanol in the presence of molecular sieves. The resulting composition is a protected pyridine-15-crown-5. The protected pyridine-15-crown-5 can be deproteced to form composition 20 by conventional methods. Composition 20 can be attached to polystyrene by reacting the composition in cesium carbonate and chloromethylpolystyrene in $THF/CH_3CN$ to form composition 21.

As a side note, the side arms can be different that that shown above. For example, —$(CH_2)_nO$—, —$(CH_2)_nN$—, or —$(CH_2)_nS$—, can be used, where n is an integer from 1 to 18. Alternatively, branched alkyl-O, branched alkyl-N, or branched alkyl-S can also be used, having from 1 to 18 carbon atoms. Additionally, the dotted lines are used to show two possible side arm linkers attaching the crown to the polystyrene. Both are provided as shown on composition 21 to denote two possible equivalent isomers. Both isomers can Enantiomeric Separations The examples which follow demonstrate how the diketo- and pyridine-containing chiral crown ether ligands (with steric hindrance or bulky groups) tethered to or coated on solid supports, and having a hydrophobic organic solvent coating thereon can be used to remove, concentrate, and/or separate target enantiomers from counter-enantiomers. The separation can be carried out as a composition of the present invention (or other composition having a selectivity of at least 4) having an affinity for the target enantiomer being placed in a column. An aqueous source solution containing a mixture (usually a racemic mixture) of target enantiomers and counter-enantiomers is then passed through the column.

The flow rate for the solution may be increased by applying pressure with a pump on the top or bottom of the column or applying a vacuum in the receiving vessel. After the source solution has passed through the column and a greater percentage of the counter-enantiomer present in the raffinate is removed, a much smaller volume of a recovery solution (receiving liquid) is used to collect the target enantiomer in a more purified form. Any receiving solution known by those skilled in the art can be used, provided it is functional with the present invention. This describes a first stage separation. In second or third stage separations, the selectivity of the ligand-bound solid support can be reversed such that the target enantiomer can be collected in the raffinate. Though this is the preferred method, variations can be carried out as would be apparent to one skilled in the art after considering the present disclosure.

The following separation examples are illustrative only and are not comprehensive of the many separations of target enantiomers over counter-enantiomers that are possible using the compositions of the present invention.

Example 5

Separation of Enantiomers of β-phenylalanine ethyl ester

In this example, 0.32 ml of the diphenyl-diketo-pyridine-18-crown-6 was coated on polystyrene, and further coated with $CH_2Cl_2$, as described in Example 4. The resulting coated ligand-bound solid support was then placed in a column. A 25° C. 3 ml racemic source solution containing 50 mMolar R and S enantiomers of the ethyl ester of β-phenylalanine, 0.01 M $HClO_4$, and 0.5 M $LiClO_4$ was drawn through the column at a 0.012 ml/min flow rate. Next, a 2 ml aqueous solution of 0.5 M $LiCO_4$ and 0.01 M $HClO_4$ was passed through the column to wash out the loading solution remaining in the column. The β-phenylalanine ester loaded on the column was then eluted in 3 ml of deionized water at 25° C. at a flow rate of from 0.01–0.02 ml/min in two 1.5 ml aliquots.

The amount of the R and S enantiomer in the aqueous eluent or stripping aliquots was then analyzed by HPLC. Analysis showed the presence of 44.3 mmoles of the S-β-phenylalanine ethyl ester and 11.1 mmoles of the R-β-phenylalanine ethyl ester in the 3 ml of water elution passed through the column. Hence, the S-β-phenylalanine ethyl ester that was bound by the column after only a single stage separation gave a purity of about 83.3% (which provides an α-value of about 5).

This example describes only a first stage of up to three (or more) separation stages. If the desire is to further purify the S-β-phenylalanine ethyl ester, or the R-β-phenylalanine ethyl ester, additional stages can be performed. For example, the enantiomers can be further purified to 96% and even to >99% if a second or third stage of separation is performed, respectively. To accomplish this, once the S-β-phenylalanine ethyl ester bound to the compositions within the separation device is contacted with the aqueous receiving solution, the additional separation stages can be carried out. Specifically, the receiving solution containing much more S-β-phenylalanine ethyl ester (about 83.3%) than the R-enantiomer is preferably ran through a column or other separation device that is configured such that the resin may selectively bind to the minority of the R-enantiomers. This can be done by providing a ligand of reverse chirality. Thus, after only this second stage, the resin, i.e. coated ligand-bound solid support, can bind the R-enantiomer producing a raffinate containing about 96% pure S-β-phenylalanine ethyl ester (based upon an α-value>5). If a third stage separation is desired, the raffinate of stage two can be run through a separation device similar to that described in stage two, purifying the third stage raffinate to >99% S-β-phenylalanine ethyl ester.

Example 6

Separation of enantiomers of naphthyl ethylamine

In this example, 4.2 mmoles of the diphenyl-diketo-pyridine-18-crown-6 ligand coated on a solid on polystyrene was prepared, and was further coated with $CH_2Cl_2$ organic solvent, as described in Example 4. Separations were carried out similar to those described in Example 5, except that the 25° C. racemic 0.7 ml source solution contained 10 mMolar R and S enantiomers of naphthyl ethyl amine (instead of the ethyl ester of the β-phenylalanine described in Example 5, and the amount of amine loaded was measured instead of the amount of elution).

After carrying out the first stage separation, HPLC analysis of the raffinate compared to the feed solution showed that 45.3% of the R-naphthyl ethylamine was bound to the ligand and ultimately separated. The selectivity or α-value was calculated to be 4.3.

While the invention has been described with reference to certain preferred embodiments, those skilled in the art will appreciate that various modifications, changes, omissions, and substitutions can be made without departing from the spirit of the invention. For example, though it can be preferred that the target enantiomer be collected at the first stage in the receiving solution, and at the subsequent stages in the raffinate, at any given stage, the separation device can be engineered such that the raffinate or the receiving solution contains the target enantiomer.

What is claimed is:

1. A composition for selectively binding an amine or amino acid target enantiomer over its counter-enantiomer, comprising:
    a solid support;
    an optically active ligand tethered to or coated on the solid support, said ligand having the structure:

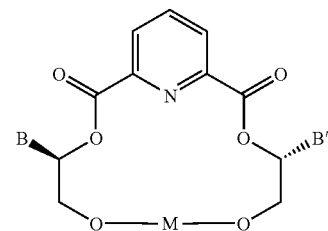

where B and B' are independently bulky groups configured to substantially allow the target enantiomer to bind to the composition, said B and B' being further configured to substantially sterically hinder the counter-enantiomer from binding to the composition; and M is saturated —C2H3— or saturated —C2H3OC2H4—when M is tethered to the solid support, or M is saturated —C2H4—0r saturated —C2H4OC2H4— when M is coated on the solid support; and a hydrophobic organic solvent coating coated on the solid support.

2. A composition as in claim 1, wherein B and B' are independently selected from the group consisting of aromatic, lower branched alkyl having from 3 to 10 carbon atoms, and lower straight alkyl having from 3 to 10 carbon atoms.

3. A composition as in claim 2, wherein B and B' are independently selected from the group consisting of naphthyl, pyridyl, anthracyl, phenanthryl, benzonaphthyl, phenyl, and combinations thereof.

4. A composition as in claim 2, wherein B and B' are phenyl.

5. A composition as in claim 2, wherein B and B' are independently lower branched alkyl having from 4 to 10 carbon atoms.

6. A composition as in claim 5, wherein B and B' are t-butyl.

7. A composition as in claim 1, wherein the hydrophobic organic solvent is selected from the group consisting of methylene chloride, chloroform, dichloroethane, benzene, toluene, xylene, hexane, octane, and combinations thereof.

8. A composition as in claim 1, wherein the solid support is a porous or non-porous organic polymer.

9. A composition as in claim 1, wherein the solid support is a porous or non-porous inorganic particulate.

10. A composition as in claim 1, wherein the optically active ligand is coated on the solid support.

11. A composition as in claim 10, wherein the hydrophobic organic solvent is coated over the optically active ligand after the optically active ligand is coated on the solid support.

12. A composition as in claim 10, wherein the hydrophobic organic solvent and the optically active ligand are coated on the solid support as a single coating.

13. A composition as in claim 1, wherein the optically active ligand is a diketo-pyridine-15-crown-5.

14. A composition as in claim 1, wherein the optically active ligand is a diketo-pyridine-18-crown-6.

15. A composition as in claim 1, wherein the optically active ligand is tethered to the solid support, and the composition is defined by the structure:

SS-A-X-L wherein SS is the solid support, said solid support being a porous or non-porous inorganic particulate or organic polymer, A is a covalent linkage mechanism, X is a hydrophilic spacer grouping, and L is the optically active ligand, with the proviso that when SS is the organic polymer, A-X may be combined as a single covalent linkage.

16. A composition as in claim 15, wherein SS is an organic polymer solid support selected from the group consisting of polyacrylate, polystyrene, polyphenol, and combinations thereof.

17. A composition as in claim 16, wherein A and X are combined and are represented by the formula:

—(CH$_2$)$_x$—(Y)$_y$—(CH$_2$)$_z$— where y is 0 or 1; x and z are independently 0 or integers from 1 to 10; and Y is member selected from the group consisting of O, S, C=N, CO, CONH, CSNH, COO, CSO, NH, N-lower alkyl, SO, SO$_2$, SO$_2$NH, C$_6$H$_4$ and CH$_2$C$_6$H$_4$, with the proviso that at least one of x, y, and z must be at least 1.

18. A composition as in claim 15, wherein SS is an inorganic solid support selected from the group consisting of sand, silica gel, glass, glass fibers, alumina, zirconia, titania, nickel oxide, and combinations thereof.

19. A composition as in claim 18, wherein A is —Si(Z, Z')-0-, wherein Z and Z' are independently selected from the group consisting of Cl, Br, I, lower alkyl, lower alkoxy, substituted lower alkyl, substituted lower alkoxy, and 0-bound to SS.

20. A composition as in claim 18, wherein X is represented by the formula:

(CH$_2$)$_a$, (OCH$_2$CHR$^1$CH$_2$)$_b$ wherein R1 is a member selected from the group consisting of H, SH, OH, lower alkyl, and aryl; a is an integer from 3 to 10; and b is 0 or 1.

21. A method for concentrating, removing, and separating an amine or amino acid target enantiomer from its counter-enantiomer present in a source solution containing an enantiomeric mixture comprising the steps of:
(a) contacting the source sdution with a composition having the structure:
(i) a solid support;
(ii) an optically active ligand tethered to or coated on the solid support having the structure:

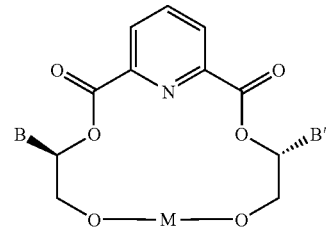

where B and B' are independently bulky groups; and M is saturated —C$_2$H$_3$— or saturated —C$_2$H$_3$OC$_2$H$_4$— when M is tethered to the solid support, or M is saturated —C$_2$H$_4$— or saturated —C$_2$H$_4$OC$_2$H$_4$— when M is coated on the solid support; and
(iii) a hydrophobic organic solvent coating, wherein the composition has an affinity for the amine or amino acid target enantiomer over its counter-enantiomer, and wherein upon contacting, the target enantiomer is preferentially complexed to the composition;
(b) removing the source solution from contact with the composition to which has the target enantiomer has been complexed;
(c) contacting the composition having the target enantiomer complexed thereto with a second volume of an aqueous receiving solution such that the target enantiomer is separated from the composition; and
(d) recovering the target enantiomer in concentrated form in the receiving solution.

22. A method as in claim 21, wherein the target enantiomer is substantially soluble in the receiving solution, and (i) the receiving solution has greater affinity for the target enantiomer than does the composition, (ii) the receiving solution has a greater affinity for the composition than does the target enantiomer, or (iii) the receiving solution eliminates the binding strength or mechanism of binding of the target enantiomer to the composition, thereby quantitatively stripping the target enantiomer from the ligand.

23. A method as in claim 21, wherein B and B' are configured to allow the target enantiomer to bind to the composition, said B and B' being further configured to substantially sterically hinder the counter-enantiomer from binding to the composition.

24. A method as in claim 21, wherein B and B' are independently selected from the group consisting of aromatic, lower branched alkyl having from 3 to 10 carbon atoms, and lower straight alkyl having from 3 to 10 carbon atoms.

25. A method as in claim 21, wherein the hydrophobic organic solvent is selected from the group consisting of methylene chloride, chloroform, dichloroethane, benzene, toluene, xylene, hexane, octane, and combinations thereof.

26. A method as in claim 21, wherein the solid support is an organic polymer selected from the group consisting of polyacrylate, polystyrene, and polyphenol, and combinations thereof.

27. A method as in claim 21, wherein the solid support is an inorganic solid support selected from the group consisting of sand, silica gel, glass, glass fibers, alumina, zirconia, titania, nickel oxide and combinations thereof.

28. A method as in claim 21, wherein the ligand is coated on the solid support.

29. A method as in claim 28, wherein the hydrophobic organic solvent is coated over the ligand after the ligand is coated on the solid support.

30. A method as in claim 28, wherein the hydrophobic organic solvent and the ligand are coated on the solid support as a single coating.

31. A method as in claim 21, wherein the optically active ligand is a diketo-pyridine-15-crown-5.

32. A method as in claim 21, wherein the optically active ligand is a diketo-pyridine-18-crown-6.

33. A method as in claim 21, wherein the target enantiomer and its counter-enantiomer is a β-amino acid.

34. A method as in claim 21, wherein the target enantiomer and its counter-enantiomer is an aromatic α-amine.

35. A non-chromatographic method of separating an enantiomeric molecule from its counter-enantiomer, comprising:
   (a) flowing a racemic feed solution containing a target enantiomer and its counter-enantiomer through a separation device, said separation device including a first composition comprising:
      (i) a solid support;
      (ii) an optically active ligand tethered to or coated on the solid support having the structure of Formula 1 below:

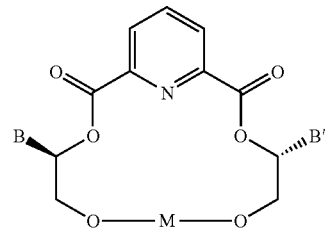

Formula 1 where B and B' are independently bulky groups; and M is saturated $-C_2H_3-$ or saturated $-C_2H_3OC_2H_4-$ when M is tethered to the solid support, or M is saturated $-C_2H_4-$ or saturated $-C_2H_4OC_2-$ when M is coated on the solid support; and (iii) a hydrophobic organic solvent coating, wherein the first composition has an affinity for the target enantiomer and a selectivity of at least 4;
   (b) selectively forming a complex between the target enantiomer and the first composition, thereby forming a first raffinate having increased purity of the counter-enantiomer;
   (c) breaking the complex between the target enantiomer and the first composition with a second volume of an aqueous receiving solution to form a target enantiomer enhanced receiving liquid;
   (d) flowing the target enantiomer enhanced receiving liquid through a second separation device, said second separation device including a second composition having the structure of Formula 1, but having an opposite optical activity with respect to the first composition; and
   (e) selectively forming a complex between the counter-enantiomer and the second composition in the second separation device, thereby forming a second raffinate having increased purity of the target enantiomer.

* * * * *